US00PP22200P2

(12) United States Plant Patent
Tristram

(10) Patent No.: US PP22,200 P2
(45) Date of Patent: Oct. 18, 2011

(54) ***EUPHORBIA* PLANT NAMED 'WALEUPHGLO'**

(50) Latin Name: *Euphorbia amygdaloides*
Varietal Denomination: WALEUPHGLO

(76) Inventor: David Tristram, Arundel (GB)

( * ) Notice: Subject to any disclaimer, the term of this patent is extended or adjusted under 35 U.S.C. 154(b) by 0 days.

(21) Appl. No.: 12/803,633

(22) Filed: Jun. 30, 2010

(51) Int. Cl.
*A01H 5/00* (2006.01)

(52) U.S. Cl. ..... Plt./302

(58) Field of Classification Search ..... Plt./302
See application file for complete search history.

*Primary Examiner* — Annette Para

(57) ABSTRACT

A new cultivar of *Euphorbia* plant named 'WALEUPHGLO' that is distinguishable by stout compact-spreading habit, bright ruby-red foliage in spring and summer, and contrasting cherry-red stems. In combination these traits set 'WALEUPHGLO' apart from all other existing varieties of *Euphorbia* known to the inventor.

2 Drawing Sheets

Genus: *EUPHORBIA*.
Species: *amygdaloides*.
Denomination: 'WALEUPHGLO'.

BACKGROUND OF THE INVENTION

The present invention relates to a new and distinct cultivar of spurge, an ornamental shrub suitable for use in garden border, modern landscape, or container. The new invention, in the Euphorbiaceae family, is known botanically as *Euphorbia amygdaloides* and will be referred to hereinafter by the cultivar name 'WALEUPHGLO'.

'WALEUPHGLO' was discovered as a naturally occurring whole plant mutation derived from the parent an individual *Euphorbia amygdaloides* 'Purpurea' (unpatented). The inventor discovered 'WALEUPHGLO' at the inventor's nursery in Walberton, West Sussex, United Kingdom, and selected 'WALEUPHGLO' in the summer of 2006 from a growing crop of *Euphorbia amygdaloides* 'Purpurea'. The closest comparison plant is *Euphorbia amygdaloides* 'Purpurea'. 'WALEUPHGLO' is distinguishable from 'Purpurea' by foliage color.

'WALEUPHGLO' is robust, exhibiting a long period of seasonal interest, with bright ruby-red foliage, contrasting cherry-red stems, stout compact-spreading habit, and masses of chartreuse bracts from early summer through fall. Drought tolerant once established 'WALEUPHGLO' grows to within the range of 46-50 cm. in height and within the range of 50-76 cm. in width. Cultural requirements include moderate to full sun, well-draining soil, and moderate to minimal water. Full sun enhances the rich foliage color. 'WALEUPHGLO' is hardy in USDA Zones 6-11.

The first asexual reproduction of 'WALEUPHGLO' was conducted in 2006. Asexual propagation was accomplished by the inventor in West Sussex, United Kingdom using the method of tip cuttings. Since then the new *Euphorbia* cultivar named 'WALEUPHGLO' has been determined stable, fixed, and reproduces true to type in successive generations of asexual propagation.

SUMMARY OF THE INVENTION

The following traits have been repeatedly observed and represent the distinguishing characteristics of 'WALEUPHGLO'. These traits in combination distinguish 'WALEUPHGLO' from all other existing varieties of *Euphorbia* known to the inventor. 'WALEUPHGLO' has not been tested under all possible conditions and phenotypic differences may be observed with variations in environmental, climatic, and cultural conditions, however, without any variance in genotype.

1. 'WALEUPHGLO' exhibits stout compact-spreading habit.
2. 'WALEUPHGLO' exhibits bright ruby-red foliage.
3. 'WALEUPHGLO' exhibits contrasting cherry-red stems.
4. 'WALEUPHGLO' exhibits masses of chartreuse bracts.
5. 'WALEUPHGLO' blooms from early summer through fall.
6. 'WALEUPHGLO' is hardy in USDA Zones 6-11.
7. 'WALEUPHGLO' reaches a range of 46-50 cm. in height and 50-76 cm. in width at maturity.

BRIEF DESCRIPTION OF THE DRAWINGS

The accompanying color drawings illustrate the overall appearance of 'WALEUPHGLO' showing color as true as it is reasonably possible to obtain in color reproductions of this type. Color in the drawings may differ from the color values cited in the detailed botanical description, which accurately describe the actual color of the new variety 'WALEUPHGLO'.

The drawing labeled

The drawing labeled

Figure 1:
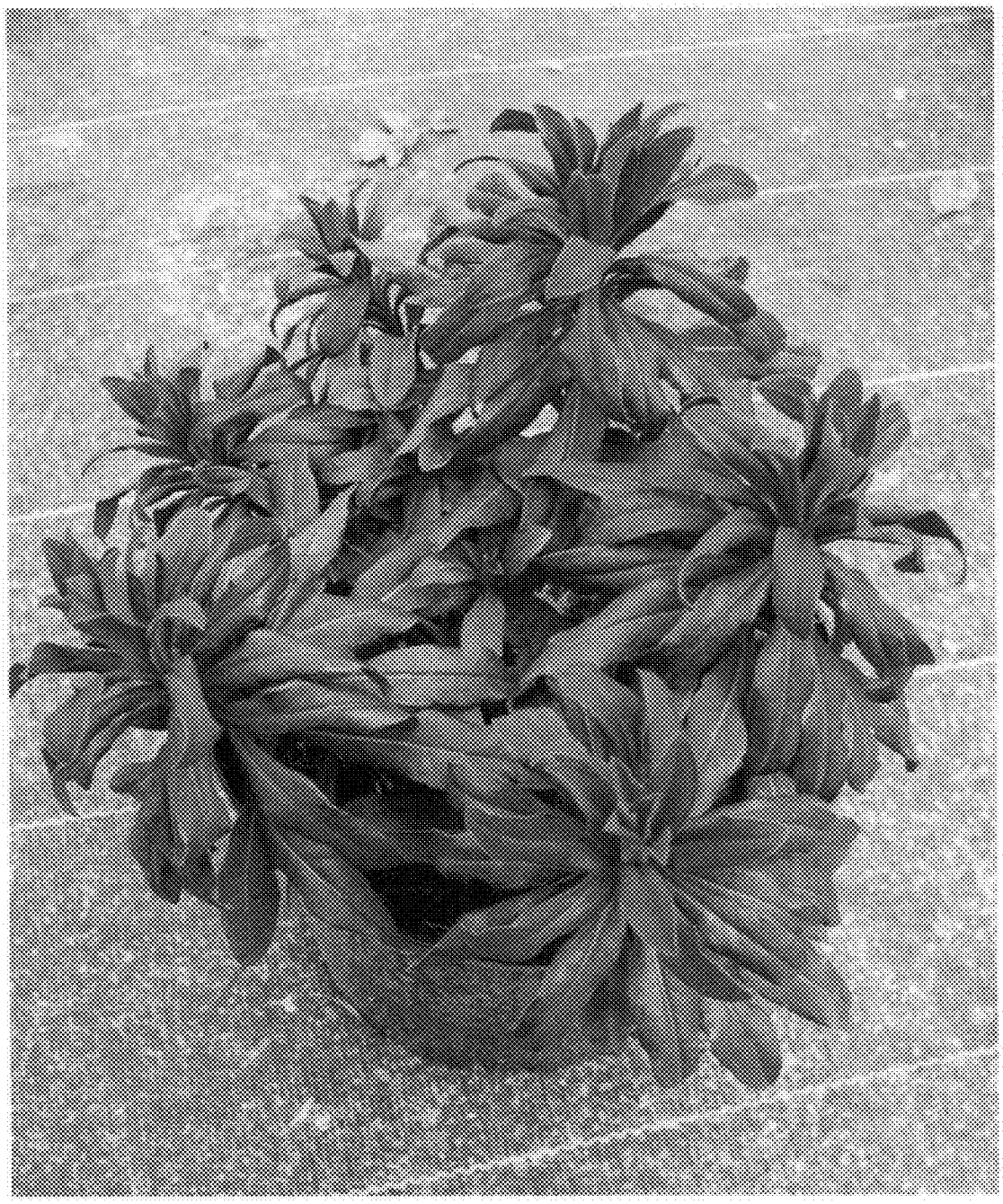
FIG. 1 depicts the early spring flush of growth of 'WALEUPHGLO'
Figure 2:
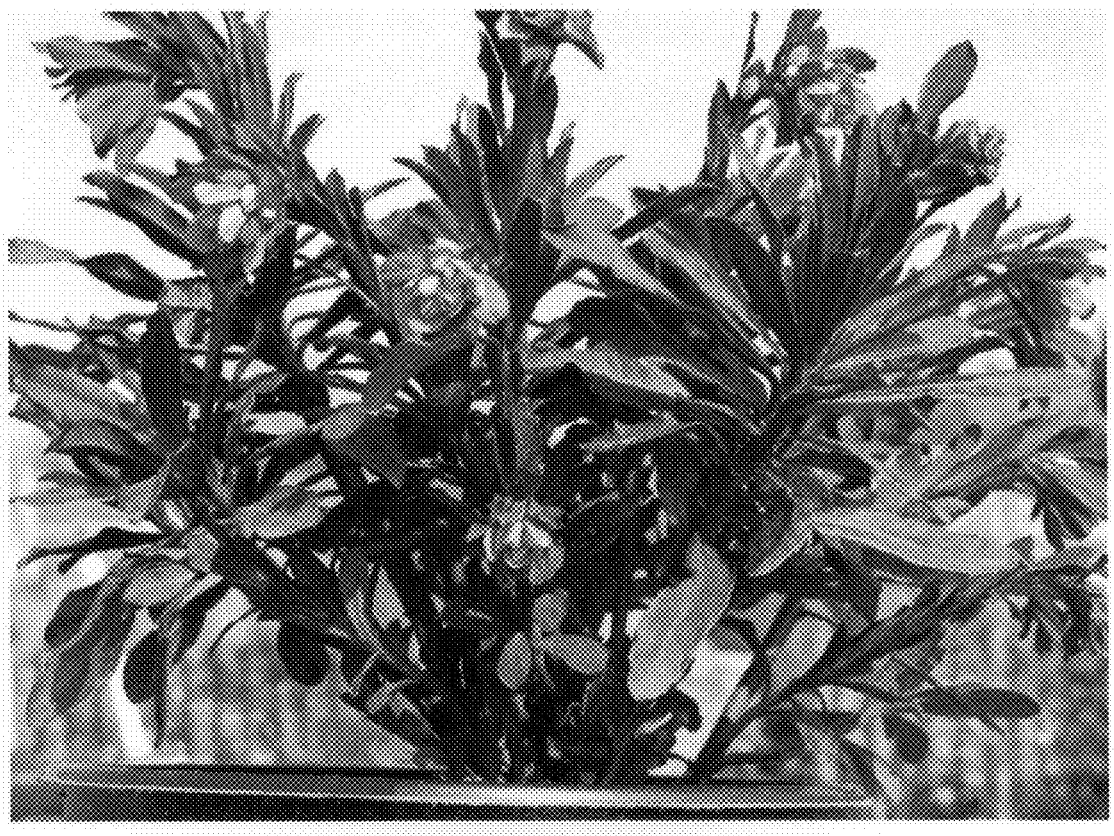
FIG. 2 depicts the emerging inflorescences of 'WALEUPHGLO', in early summer.

Both drawings were made from one year old plants which have been grown out of doors in West Sussex, England. Although flower and foliage color may appear different from actual color due to light reflectance, they are as accurate as possible by conventional photography.

BOTANICAL DESCRIPTION OF THE PLANT

The following is a detailed botanical description of 'WALEUPHGLO'. Observations, measurements, values and comparisons were collected in Arroyo Grande, Calif. from a 9-month-old 1-liter container plant grown out-of-doors.

Color determinations are made in accordance with the 2001 edition of The Royal Horticultural Society Colour Chart of London, England, except where general color terms of ordinary dictionary significance are used. The growing requirements of the new variety are similar to the species.

Botanical classification: *EUPHORBIA amygdaloides* 'WALEUPHGLO'.

Family: Euphorbiaceae.

Genus: *EUPHORBIA*.

Species: *amygdaloides*.

Denomination: 'WALEUPHGLO'.

Common name: Spurge.

Commercial classification: Ornamental shrub.

Parentage: *EUPHORBIA amygdaloides* 'WALEUPHGLO' was discovered as a naturally occurring whole plant mutation derived from the parent an individual *Euphorbia amygdaloides* 'Purpurea' (unpatented).

Asexual propagation method: Tip cuttings.

Rooting habit: Fine and fibrous.

Time to develop roots: 6-8 weeks are needed for roots to develop on an initial cutting.

Rooting temperature recommended to develop roots: 18-22° Centigrade in hoop house.

Crop time: 6-8 weeks to produce a finished 4-inch container plant from 72 cell transplant, and 10-12 weeks to produce a 1-liter container plant from 72 cell transplant.

Habit: Stout compact-spreading.

Use: Garden border, modern landscape, and container.

Type: Perennial.

Vigor: Robust.

First season plant dimensions (range): 30-35 cm. in height and 20-25 cm. in width.

Mature plant dimensions (range): 40-50 cm. in height and 50-55 cm. in width.

Cultural requirements: Moderate to full sunlight, well-draining porous commercial medium and moderate to minimal water. Maintain dry for over-wintering. Soil pH: 5.8-6.2.

Disease and pest susceptibility: Susceptible to mites, botrytis and powdery mildew.

Hardiness: Hardy in USDA Zones 6-11.

Vernalization: None necessary.

Seasonal traits: Bright ruby-red foliage color in spring and summer; chartreuse bracts summer through fall.

Special considerations: Drought tolerant once established. Hazardous. All parts exude a white milky substance when bruised that is poisonous if ingested, and may elicit dermal irritation.

Growing recommendations: Prune flowering stem hard back to the base after blooming has finished. Full sun brings out best spring flushing color.

Stem:

- *Branching habit.*—Divergent.
- *Stem quantity* (*average*).—19 per 1-liter container plant.
- *Dimensions* (*average*).—13 cm. in length and 0.50 cm. in diameter.
- *Shape.*—Columnar.
- *Surface.*—Pubescent.
- *Color.*—187B.
- *Internode length* (*range*).—0.50 cm. to 2 cm.
- *Fragrance.*—Pungent when bruised.

Foliage:

- *Type.*—Evergreen.
- *Arrangement.*—Whorled.
- *Division.*—Simple.
- *Shape.*—Obovate.
- *Length* (*range*).—4.50 cm. to 6.90 cm.
- *Width* (*range*).—1.40 cm. to 1.80 cm.
- *Leaf apex.*—Subacute.
- *Leaf base.*—Attenuate.
- *Quantity* (*average*).—35 leaves per stem.
- *Venation pattern* (*abaxial and adaxial surfaces*).—Pinnate with prominent mid-vein.
- *Vein color* (*adaxial surface*).—185A.
- *Vein color* (*abaxial surface*).—185A.
- *Margin.*—Entire.
- *Surface* (*adaxial surface*).—Puberulent.
- *Surface* (*abaxial surface*).—Puberulent.
- *Attachment.*—Sessile.
- *Leaf color, spring and early summer growth, adaxial surface.*—184D.
- *Leaf color, spring and early summer growth, adaxial surface.*—46D.
- *Leaf color, after flowering and into fall* (*both surfaces*) .—N186D aging to N186C.
- *Leaf color, oldest leaves during winter.*—147A.
- *Leaf fragrance.*—Pungent when bruised.

Flower:

- *Blooming season.*—Early summer through fall.
- *Type of inflorescence.*—Cyathium.
- *Inflorescence shape.*—Cupule.
- *True perianth.*—Absent.
- *Staminate flower.*—Apetalous.
- *Pistillate flower.*—Apetalous.
- *Cyathia quantity* (*average per* 1-*liter*): >50.
- *Cyathia quantity* (*average per rachis*): 4.
- *Cyathium dimensions.*—1.50 cm. in depth and 2 cm. in diameter.
- *Aspect.*—Facing upward and outward.
- *Bud shape* (*range*).—Ovoid to globose.
- *Bud dimensions* (*average*).—1 mm. in height and diameter.
- *Bud surface.*—Glabrous.
- *Bud color.*—185A.
- *Bud apex.*—Rounded.
- *Rachis color.*—187B.
- *Rachis dimensions* (*average*).—5 cm. in length and 1 mm. in diameter.
- *Rachis shape.*—Cylindrical.
- *Rachis surface.*—Glabrous.
- *Bract quantity* (*range*).—4-8 per rachis.
- *Bract fused or unfused.*—Unfused.
- *Bract color* (*adaxial surface*).—N144A.
- *Bract color* (*abaxial surface*).—185A.
- *Bract margin.*—Entire.
- *Bract shape.*—Orbicular.
- *Bract apex.*—Obtuse.
- *Bract base.*—Rounded.
- *Bract dimensions.*—1 cm. in length and 1.10 cm. in width.
- *Bract surfaces* (*adaxial and abaxial*).—Glabrous.
- *Lastingness of cyathium* (*range*).—20-35 days.
- *Cyathium fragrance.*—Pungent odor when bruised.

Reproductive organs:

- *Stamens* (*average*).—4 in number.
- *Stamen color.*—N144A.
- *Stamen length.*—3 mm.
- *Pollen color.*—14A.
- *Pollen quantity.*—Minimal.
- *Pistil.*—1 in number.
- *Pistil length* (*average*).—4 mm.

*Pistil color.*—185A.
*Style length.*—<1 mm.
*Style color.*—185A.
*Stigma color.*—185A.
*Stigma shape.*—Bi-fid.
*Stigma width.*—<1 mm.
*Ovary shape.*—Globular.
*Ovary dimensions.*—2 mm. in height and 2 mm. in diameter.
*Ovary color.*—185A.
*Ovary position.*—Superior.
*Nectary.*—5 in number.
*Nectary color.*—N144A.
*Nectary dimensions.*—2 mm. in width and <1 mm. in length.

Seed: No seed has been observed to date.

The invention claim is:

1. A new and distinct cultivar of *Euphorbia* plant named 'WALEUPHGLO' as described and illustrated herein.

* * * * *